US008688618B2

(12) United States Patent
McNutt et al.

(10) Patent No.: US 8,688,618 B2
(45) Date of Patent: Apr. 1, 2014

(54) METHOD AND SYSTEM FOR DETERMINING TREATMENT PLANS

(75) Inventors: Todd R. McNutt, Severna Park, MD (US); Russell H. Taylor, Severna Park, MD (US); Michael Kazhdan, Arlington, VA (US); Binbin Wu, Odenton, MD (US); Patricio Simari, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 224 days.

(21) Appl. No.: 12/820,852

(22) Filed: Jun. 22, 2010

(65) Prior Publication Data

US 2011/0153547 A1    Jun. 23, 2011

Related U.S. Application Data

(60) Provisional application No. 61/219,458, filed on Jun. 23, 2009.

(51) Int. Cl.
  *G06F 17/00*   (2006.01)
  *G06N 7/04*    (2006.01)

(52) U.S. Cl.
  USPC .......................................................... 706/54

(58) Field of Classification Search
  USPC .......................................................... 706/52
  See application file for complete search history.

(56) References Cited

U.S. PATENT DOCUMENTS

| | | | |
|---|---|---|---|
| 5,337,231 A | 8/1994 | Nowak et al. | |
| 6,090,365 A | 7/2000 | Kaminski et al. | |
| 6,560,311 B1 | 5/2003 | Shepard | |
| 6,694,298 B1* | 2/2004 | Teagarden et al. | 705/3 |
| 7,046,762 B2 | 5/2006 | Lee | |
| 7,668,662 B2 | 2/2010 | Kroll et al. | |
| 2003/0219098 A1* | 11/2003 | McNutt et al. | 378/65 |
| 2005/0028869 A1 | 2/2005 | Roth et al. | |
| 2005/0288869 A1 | 12/2005 | Kroll et al. | |
| 2006/0050839 A1 | 3/2006 | Balan et al. | |

(Continued)

FOREIGN PATENT DOCUMENTS

WO    WO 99/62565    12/1999

OTHER PUBLICATIONS

A Shape Relationship Descriptor for Radiation Therapy Planning Medical Image Computing and Computer-Assisted Intervention—MICCAI 2009 5762: 100-108 , Jan. 1, 2009 By Kazhdan, Michael; Simari, Patricio; McNutt, Todd; Wu, Binbin; Jacques, Robert; Chuang, Ming; Taylor, Russell.*
U.S. Appl. No. 13/335,565.

(Continued)

*Primary Examiner* — Kakali Chaki
*Assistant Examiner* — Ababacar Seck
(74) *Attorney, Agent, or Firm* — DLA Piper LLP US

(57) ABSTRACT

A system and method for determining at least one new treatment plan for at least one new patient, comprising: providing at least one representation of the at least one new patient's at least one organ at risk relative to at least one target; searching for at least one prior treatment plan for at least one prior patient with at least one similar representation; and reviewing the at least one prior treatment plan for the at least one prior patient in order to determine whether the at least one new treatment plan can be improved based on information in the at least one prior treatment plan.

18 Claims, 10 Drawing Sheets

(6 of 10 Drawing Sheet(s) Filed in Color)

(56) References Cited

U.S. PATENT DOCUMENTS

2009/0316858 A1   12/2009   Nord
2010/0232572 A1*  9/2010    Nord et al. .................. 378/65
2011/0091014 A1   4/2011    Siljamaki

OTHER PUBLICATIONS

Elienne Garin et al., "Effect of a 188 Re-SSS lipiodol/131l-lipidol mixture, 188 Re-SSS lipiodol alone or 131l-lipiodol alone on the survival of rats with hepatocellular carcinoma", Nuclear Medicine Communications, vol. 27, No. 4, pp. 363-369, Apr. 2006.
A. Lechner et al., "Targeted Radionuclide therapy: theoretical study of the relationship between tumour control probability and tumour radius for a 32 P/33 P radionuclide cocktail", Physics in Medicine and Biology, vol. 53, No. 7, pp. 1961-1974, Mar. 18, 2008.
Linda Villard et al., "Cohort Study of Somatostatin-Based Radiopeptide Therapy With [90Y-DOTA]-TOC Versus [90Y-DOTA]-TOC Plus [177Lu-DOTA]-TOC in Neuroendocrine Cancers", Journal of Clinical Oncology, vol. 30, No. 10; pp. 1100-1106, Apr. 1, 2012.
Greg L. Piosker et al., "Rituximab: A Review of its Use in Non-Hodgkin's Lymphoma and Chronic Lymphocytic Leukaemia", Drugs, Vol, 63, No. 8, pp. 803-843 (2003).
Gillian M. Keating, "Spotlight on Rituximab in Chronic Lymphocytic Leukemia; Low-Grade or Follicular Lymphoma; and Diffuse Large B-Cell Lymphoma", BioDrugs, vol. 25, No. 1, pp. 55-61, Feb. 2011.
Thomas E. Witzig. "Treatment recommendations for Radioimmunotherapy in Follicular Lymphoma: A Consensus Conference Report", Leuk. Lymphoma, vol. 52, No. 7, pp. 1188-1199, Jul. 2011.
Peter Johnson et al., "The Mechanisms of Action of Rituximab in the Elimination of Tumor Cells", Seminars in Oncology, vol. 30, No. 1, Suppl 2, pp. 3-8, Feb. 2003.
Oliver W. Press et al., "Treatmnet of Refractory Non-Hodgkins's Lymphoma with Radiolabeled MB-1 (anti-CD37) Antibody". Journal of Clinical Oncology, vol. 7, No. 8, pp. 1027-1038, Aug. 1989.
Oliver W. Press et al., "Phase II Trial of 131I-B1 (anti-CD20) Antibody Therapy with Autologous Stem Cell Transplantation for Relapsed B Cell Lymphomas", The Lancet, vol. 346, No. 8971, pp. 336-340, Aug. 5, 1995.
E. Frey et al., "Estimation of Post-Therapy Marrow Dose Rate in Myeloablative Y-90 Ibritumomab Tiuxetan Therapy", J. Nucl. Med., vol. 47, No. Suppl 1, pp. 156P (2006).
Richard Wahl et al., "Organ Dosimetry Dose Escalation of Yttrium 90 Ibritumomab Tiuxetan radioimmunotherapy (90Y IT) with Stem Cell Transplantation (ASCT) in Patients with Non-Hodgkin's Lymphoma (NHL)", The Journal Nuclear Medicine, vol. 47, Supplement 1, pp. 97P (2006), (2 pages).
Ian M. Besse et al., "Modeling Combined Radiopharmaceutical Therapy: A Linear Optimization Framework", Technology in Cancer Research and Treatment, vol. 8, No. 1, pp. 51-60, Feb. 2009.
Hanan Amro et al., "Methodology to Incorporate Biologically Effective Dose and Equivalent Uniform Dose in Patient-Specific 3-Dimensional Dosimetry for Non-Hodgkin Lymphoma Patients Targeted with 131I-Tositumomab Therapy", The Journal of Nuclear Medicine, vol. 51, No. 4, pp. 654-659, Apr. 2010.
Robert F. Hobbs et al., "A Treatment Planning Method for Sequentially Combining Radiopharmaceutical Therapy and External radiation Therapy". Int. J. Radiation Oncology Biol. Phys., vol. 80, No. 4, pp. 1256-1262, (2011).
Sebastien Baechler et al., "Extension of the Biological Effective Dose to the MIRD Schema and Possible Implications in Radionuclide Therapy Dosimetry", Med. Phys., vol. 35, No. 3, pp. 1123-1134, Mar. 2008.
Amr Aref et al., "Radiobiological Characterization of Two Human Chemotherapy-Resistant intermediate Grade Non-Hodgkin's Lymphoma Cell Lines", Radiation Oncology Investigations, vol. 7, pp. 158-162 (1999).
J. Van Dyk et al., "Radiation-induced Lung Damage. Dose-Time-Fractionation Considerations", Radiotherapy and Oncology, vol. 14, pp. 55-69 (1989).
Bin He et al., "Comparison of Organ Residence time estimation Methods for Radioimmunotherapy Dosimetry and Treatment Planning—Patient Studies", Med. Phys., vol. 36, No. 5, pp. 1595-1601, May 2009.
Sunil Krishnan et al., "Conformal Radiotherapy of the Dominant Liver Metastasis: A Viable Strategy for Treatment of Unresectable Chemotherapy Refractory Colorectal Cancer Liver Metastases", American Journal of Clinical Oncology, vol. 29, No. 6, pp. 562-567, Dec. 2006.
Sebastien Baechler et al., "Three-Dimensional Radiobiological Dosimetry of Kidneys for Treatment Planning in Peptide Receptor Radionuclide Therapy" Med. Phys., vol. 29, No. 10, pp. 6118-6128, Oct. 2012.
Massimiliano Pacilio et al., "A Theoretical Dose-Escalation Study Based on Biological Effective Dose in Radioimmunotherapy with (90)Y-ibritumomab Tiuxetan (Zevalin)", Eur. J. Nucl. Med, Mol. Imaging, vol. 37, pp. 862-873 (2010).
J. Kotzerke et al., "Radioimmunoconjugates in Acute Leukemia Treatment: The Future is Radiant", Bone Marrow Transplantation, vol. 36, pp. 1021-1026, Oct. 10, 2005.
J.A. O'Donoghue at al., "Relationships Between Tumor Size and Curability for Uniformly Targeted Therapy with Beta-Emitting Radionuclides", The Journal of Nuclear Medicine, vol. 36, No. 10, pp. 1902-1909, Oct. 1995.
Jolanta Kunikowska et al., "Clinical Results of Radionuclide Therapy of Neuroendocrine Tumours with 90Y-DOTATATE and Tandem 90Y/177 Lu-DOTATATE: Which is Better Therapy Option?", Eur. J. Nucl. Med. Mol. Imaging, vol. 38, pp. 1788-1797, May 7, 2011.
Mark T. Madsen et al., "Potential Increased Tumor-Dose Delivery with Combined 131I-MIBG and 90Y-DOTATOC Treatment in Neuroendocrine Tumors. A Theoretic Model", The Journal of Nuclear Medicine, vol. 47, No. 4, pp. 660-667, Apr. 2006.
Thomas A. Davis et al., "The Radiosotope Contributes Significantly to the Activity of Radioimmunotherapy", Clinical Cancer Research, vol. 10, p. 7792-7798, December 7, 2004.
Thomas E. Witzig et al., "Radomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell non-Hodgkin's Lymphoma", Journal of Clinical Oncology, vol. 20, No. 10, pp. 2453-2463, May 15, 2002.
Oliver W. Press et al. "Radiolableled -Antiboy Therapy of B-Cell Lymphoma with Autologous Bone Marrow Suppoer", The New England Journal of Medicine, vol. 329, No. 17, pp. 1219-1224. Oct. 21, 1993.
Ajay K. Gopal et al., "High-Dose [131I] Tositumomab (anti-CD20) Radioimmunotherapy and Autologous Hematopoietic Stem-Cell Transplantation for Adults ≥ 60 Years Old With Relapsed or Refractory B-Cell Lymphoma", Journal of Clinical Oncology, vol. 25, No. 11, pp. 1396-1402, Apr. 10, 2007.
Ajay K. Gopal et al., "High-Dose Radioimmunotherapy Versus Conventional High-Dose Therapy and Autologous Hematopoietic Stem Cell Transplantation for Relapsed Follicular Non-Hodgkin Lymphoma: A Multivariable Chohort Analysis", Blood, vol. 102, pp. 2351-2357, Oct. 1, 2003.
Amrita Krishnan et al., "Phase II Trial of a Transplantation Regimen of Yttrium-90 Ibritumomab Tiuxetan and High-Dose Chemotherapy in Patients with Non-Hodgkin's Lymphoma", Journal of Clinical Oncology, vol. 26, No. 1, pp. 90-95, Jan. 1, 2008.
Jane N. Winter et al., "Yttrium-90 Ibritumomab Tiuxetan Doses Calculated to Deliver up to 15 Gy to Critical Organs May Be Safely Combined With High-Dose BEAM and Autologous Transplantation in Relapsed of Refractory B-Cell Non-Hodgkin's Lymphoma", Journal of Clinical Oncology, vol. 27, No. 10, pp. 1653-1659, Apr. 1, 2009.
Hong Song et al., "Therapeutic Potential of 90Y-and 131I—Labeled Anti-CD20 Monoclonal Antibody in Treating Non-Hodgkin's

(56) References Cited

OTHER PUBLICATIONS

Lymphoma with Pulmonary Involvement: A Monte Carlo-Based Dosimetric Analysis", The Journal of Nuclear Medicine, vol. 48, No. 1, pp. 150-257, Jan. 2007.

Gregory A. Wiseman et al. "Phase I/II 90Y-Zevalin (Yttrium-90 Ibritumomab Tiuxetan, IDEC-Y2B8) Radioimmunotherapy Dosimetry Results in Relapsed of Refractory Non-Hodgkin's Lymphoma", European Journal of Nuclear Medicince, vol. 27, No. 7, pp. 766-777, Jul. 2000.

Raffaella Barone et al., "Patient-Specific Dosimetry in Predicting Renal Toxicity with 90Y-DOTATOC: Revelance of Kidney Volume and Dose Rate in Finding a Dose-Effect Relationship", The Journal of Nuclear Medicine, vol. 46, No. 1 (Suppl), pp. 99S-106S, Jan. 2005.

Barry W. Wessels et al. "MIRD Pamphlet No. 20: The Effect of Model Assumptions on Kidney Dosimetry and Response—Implications for Radionuclide Therapy", The Journal of Nuclear Medicine, vol. 49, No. 11, pp. 1884-1899, Nov. 2008.

Lidia Strigari et al., "Efficacy and Toxicity Related to Treatment of Hepatocellular Carcinoma with 90Y-SIR Spheres: Radiobiologic Consideratins", The Journal of Nuclear Medicine, vol. 51, No. 9, pp. 1377-1385, Sep. 2010.

Yuni K. Dewaraja et al., "131I-Tositumomab Radioimmunotherapy: Initial Tumor Dose—Response Results Using 3-Dimensional Dosimetry Including Raditobiologic Modeling", The Journal of Nucleear Medicine, vol. 51, No. 7, pp. 1155-1162. Jul. 2010.

Mahila E. Ferrari et al., "3D Dosimetry in Patients with Early Breast Cancer Undergoing Intraopeative Avidination for Radionuclide Therapy (IART Combined with External Beam Radiation Therapy", Eur. J. Nucl. Med. Mol. Imaging, vol. 39, pp. 1702-1711 (2012).

Marta Cremonesi et al., "Radioembolisation with 90Y-Microspheres: Dosimetric and Radiobiological Investigation for Multi-Cycle Treatment", Eur. J. Nucl. Med. Mol. Imaging, vol. 35, pp. 2088-2096 (2008).

Roger W. Howell et al., "Application of the Linear-Quadratic Model to Radioimmunotherapy: Further Support for the Advantage of Longer-Lived Radionuclides", The Journal of Nuclear Medicine, vol. 35, No. 11, pp. 1861-1869, Nov. 1994.

Siyada N.F. Rizvi et al., "Biodistribution, Radiation Dosimetry and Scouting of 90Y-Ibritumomab Tiuxetan Therapy in Patients with Relapsed B-Cell Non-Hodgkin's Lymphoma Using 89Zr-Ibritumomab Tiuxetan and PET", Eur. J. Nucl. Med. Mol. Imaging, vol. 39, pp. 512-520 (2012).

George Sgouros et al., "Patient-Specific, 3-Dimensional Dosimetry in Non-Hodgkin's Lymphoma Patients Treated with 131I-Anti-B1 Antibody: Assessment of Tumor Dose —Response", The Journal of Nuclear Medicine, vol. 44, No. 2, pp. 260-268, Feb. 2003.

Heather A. Jacene et al., "Comparison of 90Y-Ibritumomab Tiuxetan and 131I-Tositumomab in Clinical Practice". The Journal of Nuclear Medicine, vol. 48, No. 11. pp, 1767-1776, Nov. 2007.

International Search report issued in International Application PCT/US2007/085400, mailed Sep. 8, 2010.

Oliver W. Press at al, "A Phase I/II Trial of Iodine-131-tositumomab (anti-CD20),etoposide, cyclophosphamide, and Autologous Stem Cell Transplantation for Relapse B-Cell Lymphomas", Blood, vol. 96, No. 9, pp. 2934-2942, Nov. 1, 2000.

B. Emami et al., "Tolerance of Normal Tissue to Therapeutic Irradiation", Int. J. Radiation Oncology Biol. Phys., vol. 21, pp. 109-122 (1991).

Roger Dale at al., "The Radiobiology of Conventional Radiotherapy and Its Application to Radionuclide Therapy", Cancer Biotherapy & Radiopharmaceuticals, vol. 20, No. 1, pp. 47-51 (2005).

Roger Dale, "Use of the Linear-Quadratic Radiobiological Model for Quantifying Kidney Response in Targeted Radiotherapy", Cancer Biotherapy & Radiopharmaceuticals, vol. 19, No. 3, pp. 363-370 (2004).

Joseph A. O'Donoghue, "Implications of Nonuniform Tumor Doses for Radioimmunotherapy", The Journal of Nuclear Medicine, vol. 40, No. 8, pp. 1337-1341, Aug. 1999.

MIRD Pamphlet No. 21: A Generalized Schema for Radiopharmaceutical Dosimetry—Standaradization of Nomenclature, The Journal of Nuclear Medicine, vol. 50, No. 3, pp. 477-484, Mar. 2009.

Bin He at al., "A Monte Carlo and Physical Phantom Evaluation of Quantitative In-111 SPECT", Physics in Medicine Biology, vol. 50, pp. 4169-4185 (2005).

H. Malcolm Hudson et al., "Accelerated Image Reconstruction Using Ordered Subsets of Projection Data", IEEE Transactions on Medical Imaging, vol. 13, No. 4, pp. 601-609, Dec. 1994.

Dan J. Kadrmas et al., "Fast Implementations of Reconstruction-Based Scatter Compensation in Fully 3D SPECT Image Reconstruction", Phys. Med. Biol., vol. 43, No. 4, pp. 857-873, Apr. 1998.

Robert F. Hobbs et al., "Arterial Wall Dosimetry for Non-Hodgkin Lymphoma Patients Treated with Radioimmunotherapy", The Journal of Nuclear Medicine, vol. 51, No. 3, pp. 368-375, Mar. 2010.

Robert F. Hobbs et al., "$^{124}$I PET-Based 3D-RD Dosimetry for a Pediatric Thyroid Cancer Patient: Real-Time Treatment Planning and Methodologic Comparison", The Journal of Nuclear Medicine, vol. 50, No. 11, pp. 1844-1847, Nov. 2009.

Andrew R. Prideaux et al., "Three-Dimensional Radiobiologic Dosimetry: Application of Radiobiologic Modelina to Patient-Specific 3-Dimensional Imaging-Based Internal Dosimetry", The Journal of Nuclear Medicine, vol. 48, No. 6, pp. 1008-1016, Jun. 2007.

John F. Fowler, "The Linear-Quadratic Formula and Progress in Fractionated Radiotherapy", The British Journal of Radiology, vol. 62, No. 740, pp. 679-694, Aug. 1989.

William T. Millar; "Application of the Linear-Quadratic Model with Incomplete Repair to Radionuclide Directed Therapy", The British Journal of Radiology, vol. 64, No. 759, pp. 242-251, Mar. 1991.

D.J. Brenner et al,, "The Linear-Quadratic Model and Most Other Common Radiobiological Models Result in Similar Predictions of Time-Dose Relationships", Radiation Research, vol. 150, pp. 83-91 (1998).

Robert F. Hobbs et al., "Calculation of the Biological Effective Dose for Piecewise Defined Dose-Rate Fits", Med. Phys., vol. 36, No. 3, pp. 904-907, Mar. 2009.

R. G. Dale, "The Application of the Linear-Quadratic Dose-Effect Equation to Fractionated and Protracted Radiotherapy", The British Journal of Radiology, vol. 58, No. 690, pp. 515-528, Jun. 1985.

R. K. Bodey et al., "Combining Dosimetry for Targeted Radionuclide and External Beam Therapies Using the Biologically Effective Dose", Cancer Biotherapy & Radiopharmaceuticals, vol. 18, No. 1, pp. 89-97 (2003).

Rachel K. Bodey et al., "Application of the Linear-Quadratic Model to Combined Modality Radiotherapy", Int. J. Radiation Oncology Biol. Phys., vol. 59, No. 1, pp. 228-241 (2004).

D. J. Brenner et al., "Conditions for the Equivalence of Continuous to Pulsed Low Dose Rate Brachytherapy", Int. J. Radiation Oncology Biol. Phys., vol. 20, pp. 181-190, Jan. 1991.

C. Chiesa et al., "A Practical Dead Time Correction Method in Planar Activity Quantification for Dosimetry During Radionuclide Therapy", The Quarterly Journal of Nuclear Medicine and Molecular Imaging, vol. 53, No. 6, pp. 5658-5670, Dec. 2009.

G. Delpon et al., "Correction of Count Losses Due to Deadtime on a DST-XIi (SMVi-GE) Camera During Dosimetric Studies in Patients Injected with iodine-131", Physics in Medicine and Biology, vol. 47, N79-N90 (2002).

James A. Sorenson et al., "Methods of Correcting Anger Camera Deadtime Losses", Journal of Nuclear Medicine, vol. 17, No. 2, pp. 137-141 (1976).

Kenneth R. Zasadny et al. "Dead Time of an Anger Camera in Dual-Energy-Window-Acquisition Mode", Med. Phys., vol. 20, No. 4, pp. 1115-1120, Jul./Aug. 1993.

Indra J. Das et al., "Intensity-Modulated Radiation Therapy Dose Prescription, Recording, and Delivery: Patterns of Variability Among Institutions and Treatment Planning Systems", JNCI, vol. 100, Issue 5, pp. 300-307, Mar. 5, 2008.

Thomas Bortfeld et al, "Image-Guided IMRT", Springer, pp. V-XII, and 1-460, Copyright 2006.

David M. Loeb et al., "Dose-finding study of 153Sm-EDTMP in Patients with Poor-Prognosis Osteosarcoma", Cancer, vol. 115, No. 11, pp. 2514-2522, Jun. 1, 2009.

(56) References Cited

OTHER PUBLICATIONS

David M. Loeb et al. "Tandem Dosing of Samarium-153 Ethylenediamin Tetramethylene Phosphoric Acid with Stem Cell Support for Patients with High Risk Osteosarcoma", Cancer, pp. 5470-5478, Dec. 1, 2010.
Pete Anderson et al., "Samarium Lexidronam (153Sm-EDTMP): Skeletal Radiation for Osteoblastic Bone Metastases and Osteosarcoma", Expert Rev Anticancer Ther., vol. 7, No. 11, pp. 1517-1527, Nov. 2007.
I. Resche et al., "A Dose-Controlled Study of 153Sm-Ethylenediaminetetramethylenephosphonate (EDTMP) in the Treatment of Patients with Painful Bone Metastases", European Journal of Cancer, Vo. 33, No. 10, pp. 1583-1591, Sep. 1997.
Oliver Sartor et al., "Safety and Efficacy of Repeat Administration of Samarium Sm-153 Lexidronam to Patients with Metastatic Bone Pain", Cancer, vol. 109, No. 3, pp. 637-643, Feb. 1, 2007.
Oliver Sartor et al., "Samarium-153-Lexidronam Complex for Treatment of Painful Bone Metastases in Hormone-Refractory Prostate Cancer", Urology, vol. 63, No. 5, pp. 940-945, May 2004.
Aldo N. Serafmi et al., Palliation of Pain Associated with Metastatic Bone cancer Using Samarium-153 Lexidronam: A Double-Blind Placebo-Controlled Clinical Trial, Journal of Clinical Oncology, vol. 16, No. 4, pp. 1574-1581, Apr. 1998.
Peter M. Anderson et al., "Gemcitabine Radiosensitization After High-Dose Samarium for Osteoblastic Osteosarcoma", Clin Cancer Res., vol. 11, No. 19, pp. 6895-6900, Oct. 1, 2005.
Peter M. Anderson et al., High-Dose Samarium-153 Ethylene Diamine Tetramethylene Phosphonate: Low Toxicity of Skeletal Irradiation in Patients with Osteosarcoma and Bone Metastases, Journal of Clinical Oncology, vol. 20, No. 1, pp. 189-196, Jan. 1, 2002.
H. Malcolm Hudson et al., "Accelerated Image-Reconstruction Using Ordered Subsets of Projection Data", IEEE T. Med. Imaging, vol. 13, No. 4, pp. 601-609, Dec. 1994.
Robert F. Hobbs et al., "A Gamma Camera Count Rate Saturation Correction Method for Whole-Body Planar Imaging", Physics in Medicine and Biology, vol. 55, pp. 817-831, (2010).
T.S. Kehwar, "Analytical Approach to Estimate Normal Tissue Complication Probabiltiy Using Best Fit of Normal Tissue Tolerance Doses into the NTCP Equation of the Linear Quadratic Model", J. Cancer Res. Ther., vol. 1, No. 3, pp. 168-179, Sep. 2005.
Rachel K. Bodey et al., "Spatial Aspects of Combined Modality Radiotherapy", Radiotherapy and Oncology, Vo. 77, No. 3, pp. 301-309, Dec. 2005.
Yong Du et al., "Partial Volume Effect Compensation for Quantitative Brain SPECT Imaging", IEEE Transaction on Medical Imaging, vol. 24, No. 8, pp. 969-976, Aug. 2005.
Jorg. Bohsung, et al, "IMRT Treatment—A Comparitive Inter-System and Inter-Centre Planning Excercise of the QUASIMODO Group," Radiotherapy and Oncology, vol. 76, pp. 354-364 (2005).
Anders B. Jensen, et al, "Influence of Late Side-Effects Upon Daily Life After Radiotherapy for Laryngeal and Pharyngeal Cancer," Acta Oncologica, vol. 33, pp. 487-491 (1994).
Q. Wu et al., "Algorithms and Functionality of an Intensity Modulated Radiotherapy Optimization System," Med. Phys., vol. 27, pp. 701-711 (2000).
A. Brahme, "Optimization of Stationary and Moving Beam Radiation Therapy Techniques," Radiother Oncol., vol. 12, pp. 129-140 (1988).
R. Lu et al., "Reduced-Order Parameter Optimization for Simplifying Prostate IMRT Planning," Phys. Med. Biol., vol. 52, pp. 849-870 (2007).
H. T. Chung et al., "Can All Centers Plan Intensity-Modulated Radiotherapy (IMRT) Effectively? An External Audit of Dosimetric Comparisons Between Three-Dimensional Conformal Radiotherapy and IMRT for Adjuvant Chemoradiation for Gastric Cancer," Int. J. Radiat. Oncol. Biol. Phys., vol. 71, pp. 1167-1174 (2008).
M.J. Williams et al., "Multicentre Quality Assurance of Intensity-Modulated Radiation Therapy Plans: A Precursor to Clinical Trials," Australas Radiol., vol. 51, pp. 472-479 (2007).
A. S. Reese et al., "Integral Dose Conservation in Radiotherapy," Med. Phys., vol. 36, pp. 731-740 (2009).
E. Astreinidou et al., "Level II Lymph Nodes and Radiation-Induced Xerostomia," Int. J. Radiat. Oncol. Biol. Phys., vol. 58, pp. 124-131 (2004).
B.V. Asselen et al., "The Dose of the parotid Glands with IMRT for Oropharyngeal Tumors: The Effect of Reduction of Positioning Margins," Radiother Oncol., vol. 64, pp. 197-204 (2002).
K.A. Vineberg et al., "Is uniform Target Dose Possible in IMRT Plans in the Head and Neck," Int. J. Radiat. Oncol. Biol. Phys., vol. 52, pp. 1159-1172 (2002).
M.A. Hunt et al., "Geometric Factors Influencing Dosimetric Sparing of the Parotid Glands Using IMRT," Int. J. Radiat. Oncol. Biol. Phys., vol. 66, pp. 296-304 (2006).
T. Saito et al., "New Algorithms for Euclidean Distance Transformation of an n-Dimensional Digitized Picture with Applications," Pattern Recognition, vol. 27, pp. 1551-1565 (1994).
E.B. Bulter et al., "Smart (Simultaneous Modulated Accelerated Radiation Therapy) Boost: A New Accelerated Fractionation Schedule for the Treatment of Head and Neck Cancer with Intensity Modulated Radiotherapy," Int. J. Radiat. Oncol. Biol. Phys., vol. 45, pp. 21-32 (1999).
A. Eisbruch et al., Phase Study of Conformal and Intensity Modulated Irradiation for for Propharyngeal Cancer. (Radiation therapy oncology group 0022, 2004).
L.B. Harrison et al., "Detailed Quality of Life Assessment in Patients Treated with Primary Radiotherapy for Cancer of the Base of Tongue," Head & Neck, vol. 19, pp. 169-175 (1997).
K. Bjordal et al., "Quality of Life in Patients Treated for Head and Neck Cancer: A Follow-Up Study 7 to 11 Years After Radiotherapy," Int. J. Radiat. Oncol. Biol. Phys., vol. 28, pp. 847-856 (1994).
U.S. Appl. No. 12/514,853.
Mihael Ankerst et al., "3d Shape Histograms for Similarity Search and Classification in Saptial Databases", Proc. 6th International Symposium on Spatial Databases (SSD'99), Hong Kong, China, Lecture Notes in Computer Science, pp. 207-226, Jul. 1999.
Paul J. Besl, "Triangles as a Primary Representation", Object Representation in Computer Vision, Lecture Notes in Computer Science, vol. 994, pp. 191-206 (1995).
Cha Zhang, "Project—3D Model Retrieval", http://amp.ece.cmu.edu/projects/3DModelRetrieval/, Nov. 2, 2002 (6 pages).
Ding-Yun Chen et al., "On Visual Similarity Based 3D Model Retrieval", Computer Graphics Forum (EUROGRAPHICS 2003), vol. 22, No. 3, pp. 223-232 (2003).
R.E. Drzymala, "Dose-Volume Histograms", International Journal of Radiation Oncology, Biology, Physics, vol. 21, No. 1, pp. 71-78 (1991).
Andrea Frome et al., "Recognizing Objects in Range Data Using Regional Point Descriptors", Computer Vision (ECCV 2004), Lecture Notes in Computer Science, vol. 3023, pp. 224-237 (2004).
Thomas Funkhouser et al., "A Search Engine for 3D Models", ACM Transactions on Graphics (TOG), vol. 22, Issue 1, pp. 83-105, Jan. 2003.
Timothy Gatzke et al., "Curvature Maps for Local Shape Comparison", In Shape Modeling International, pp. 244-253 (2005).
James Gain et al., "Fast Polygon Mesh Querying by Example", ACM SIGGRAPH'99 Conference Abstracts and Applications, pp. 241, Aug. 1999.
Berthold K.P. Horn, "Extended Gaussian Images", Proceedings of the IEEE, vol. 72, No. 12, pp. 1671-1686, Dec. 1984.
Andrew Edie Johnson et al., "Efficient Multiple Model Recognition in Cluttered 3-D Scenes", Proc. IEEE Conference on Computer Vision and Pattern, pp. 671-677 (1998).
A.E. Johnson et al., "Using Spin-Images for Efficient Multiple Model Recognition in Cluttered 3D Scenes", IEEE Transactions on Pattern Analysis and Machine Intelligence, vol. 21, Issue 5, pp. 433-449, May 1999.
Michael Kazhdan et al., "A Reflective Symmetry Descriptor", ECCV 2002, LNCS 2351, pp. 642-656 (2002).
Robert Osada et al., "Matching 3D Models with Shape Distributions", International Conference on Shape Modeling and Applications (SMI 2001), pp. 154-166, May 2001.

(56) References Cited

OTHER PUBLICATIONS

Robert Osada et al., "Shape Distributions", ACM Transactions on Graphics, vol. 21, No. 4, p. 807-832, Oct. 2002.

"3D Model Search Engine", http://shape.cs.princeton.edu/search.html, Nov. 2001 (1 page).

Yossi Rubner et al., "The Earth Mover's Distance as a Metric for Image Retrieval", International Journal of Computer Vision, vol. 40, No. 2, pp. 99-121 (2000).

Dietmar Saupe et al., "3D Model Retrieval with Spherical Harmonics and Moments", DAGM 2001, LNCS 2191, pp. 392-397 (2001).

Sen Wang et al., "Conformal Geometry and its Applications on 3D Shape Matching, Recognition, and Stitching", IEE Transactions on Pattern Analysis and Machine Intelligence, vol. 29, No. 7, pp. 1209-1220, Jul. 2007.

Jaun Zhang et al., "Retrieving Articulated 3-D Models Using Medical Surfaces and Their Graph Spectra", EMMCVPR 2005, LNCS 3757, pp. 285-300 (2005).

Avraham Eisbruch et al., "Multi-Institutional Trial of Accelerated Hypofractionated Intensity-Modulated Radiation Therapy for Early-Stage Oropharyngeal Cancer (RTOG 00-22)", International Journal of Radiation Oncology, Biology, Physics, vol. 76, No. 5, pp. 1333-1338, Apr. 2010.

Binbin Wu et al., "Patient Geometry-Driven Information retrieval for IMRT Treatment Plan Quality Control", Med. Phys., vol. 36, No. 12, pp. 5497-5505, Dec. 2009.

Mark S. Kaminiski et al., "Pivotal Study to Iodine I 131 Tositumomab for Chemotherapy-Refractory Low-Grade or Transformed Low-Grade B-Cell Non-Hodgkin's Lymphomas", Journal of Clinical Oncology., vol. 19, No. 19, pp. 3918-3928, Oct. 1, 2001.

Julie M. Vose et al., "Multicenter Phase II Study of Iodine-131 Tositumomab for Chemotherapy-Relapsed/Refractory Low-Grade and Transformed Low-Grade B-Cell Non-Hodgkin's Lymphomas", Journal of Clinical Oncology, vol. 18, No. 6, pp. 1316-1323, Mar. 2000.

Kenneth F. Koral et al., "Volume Reduction Versus Radiation Dose for Tumors in Previously Untreated Lymphoma Patients Who Received Iodine-131 Tositumomab Therapy: Conjugate Views Compared With A Hybrid Method", Cancer, vol. 94, No. 4 (Suppl), pp. 1258-1263, Feb. 15, 2002.

Susan J. Knox et al., "Yttrium-90-Labeled Anti-CD20 Monoclonal Therapy of Recurrent B-Cell Lymphoma", Clinical Cancer Research, vol. 2, pp. 457-470, Mar. 1996.

Mark S. Kaminski et al., "Radioimmunotherpay of B-cell lymphoma with [131I]anti-B1 (anti-CD20) antibody", The New England Journal of Medicine. vol. 329, No. 7, pp. 459-465, Aug. 12, 1993.

Mark S. Kaminski et al., "Radioimmunotherapy with iodine 131I tositumomab for relapsed or refractory B-cell non-Hodgkin lymphoma: updated results and long-term follow-up of the University of Michigan experience", Blood, vol. 96, No. 4, pp. 1259-1266, Aug. 15, 2000.

Mark S. Kaminski et al., "131I-tositumornab therapy as initial treatment for follicular lymphoma", The New England Journal of Medicine, vol. 352, No. 5, pp. 441-449, Feb. 3, 2005.

Thomas E. Witzig et al., "Treatment with Ibitrumomab Tiuxetan Radioimmunotherapy in Patients with Rituximab-Refractory Follicular Non-Hodgkin's Lymphoma", Journal of Clinical Oncology, vol. 20, No. 15, pp. 3262-3269, Aug. 1, 2002.

Raymond R. Raylman et al., "Magnetically enhanced radionuclide therapy", Journal of Nuclear Medicine, vol. 35, No. 1, pp. 157-163, Jan. 1994.

Donald J. Buchsbaum et al., "Improved delivery of radiolabeled anti-B1 monoclonal antibody to Raji lymphoma xenografts by predosing with unlabeled anti-B1 monoclonal antibody", Cancer Research, vol. 52, pp. 637-642, Feb. 1, 1992.

Kenneth F. Koral, "CT-SPECT fusion plus conjugate views for determining dosimetry in iodine-131-monoclonal antibody therapy of lymphoma patients", The Journal of Nuclear Medicine, vol. 35, No. 10, pp. 1714-1720, Oct. 1994.

T.E. Wheldon et al., "The curability of tumours of differing size by targeted radiotherapy using 131I or 90Y", Radiotherapy and Oncology, vol. 21, pp. 91-99. (1991).

Raymond R. Raylman et al., "Magnetically-enhanced radionuclide therapy (MERIT): in vitro evaluation", Int. J. Radiation Oncology Biol. Phys., vol. 37, No. 5, pp. 1201-1206 (1997).

Raymond R. Raylman et al., "Magnetically enhanced protection of bone marrow from beta particles emitted by bone-seeking radionuclides: theory of application", Medical Physics, vol. 22, No. 8, pp. 1285-1292, Aug. 1995.

Raya S. Brown et al., "Intra-tumoral microdistribution of 131I-labelled in patients with B-cell lymphoma following radioimmunotherapy", Nuclear Medicine & Biology, vol. 24, pp. 657-663, (1997).

S. Piantadosi et al., "Practical implementation of a modified continual reassessment method for dose-finding trials", Cancer Chemother Phamacol, vol. 41, pp. 429-436 (1998).

G.A. Wiseman et al., "Radiation dosimetry results from a Phase II trial of ibitrumomab tiuxetan (Zevalin) radioimmunotherapy for patients with non-Hodgkin's lymphoma and mild thrombocytopenia", Cancer Biotherapy & Radiopharmaceuticals, vol. 18, No. 2, pp. 165-178, Apr. 2003.

Richard L. Wahl et al., "Patient-Specific Whole-Body Dosimetry: Principles and a Simplified Method for Clinical Implementation", The Journal of Nuclear Medicine, vol. 39, No. 8 (Suppl), pp. 14S-20S, Aug. 1998.

U.S. Appl. No. 12/690,471.
U.S. Appl. No. 12/687,670.

* cited by examiner

For parallel organs, OAR2 (red) is more easily spared.
For serial organs, OAR1 (blue) is more easily spared.

METHOD AND SYSTEM FOR DETERMINING TREATMENT PLANS

This application is based on and derives the benefit of the filing date of U.S. Provisional Patent Application No. 61/219,458, filed Jun. 23, 2009. The entire content of this application is herein incorporated by reference in its entirety.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

Shape-Based Retrieval of Prior Patients Information

In the treatment of patients with malignant tumors, the goal of intensity-modulated radiation therapy is to deliver a high dose of radiation to the tumor volume while sparing adjacent organs at risk. In practice, a patient is imaged under a computed tomography (CT) scanner, the scan is segmented to identify the primary tumor volume and organs at risk, and the segmented scan is used by a dosimetrist to determine the best set of multi-leaf collimator settings to deliver a set of intensity modulated megavoltage x-ray beams targeting the tumor. Restricted by a set of physician-driven constraints (e.g., at least 95% of the tumor volume should receive a dosage of at least 70 Gy, no more than 60% of the parotid should receive more than 30 Gy, no part of the spinal cord should receive more than 45 Gy), the dosimetrist uses treatment planning software to optimize the intensity distribution for each of a set of beams according to an objective function, derived from the physician's constraints. This objective function tells the software how to score the tradeoffs between target coverage and normal tissue sparing. The system thus finds the set of multi-leaf collimator settings resulting in a dose distribution that maximizes the dose to the tumor while minimizing harmful radiation to unaffected organs.

When designing the treatment plan, it is helpful to define a shape metric that captures not only the geometries of the primary tumor volume and organs at risk (OARs), but also their configurations relative to each other. For each organ at risk, the distribution of the organ's volume relative to the primary tumor volume (e.g., the distribution of distances of points in an organ from the tumor) can be described. Since these distributions encode the distance between the organs at risk and the tumor volume, and since the spareability of an organ depends on its proximity to the irradiated tumor, these descriptors can provide a simple shape signature that helps find treatment plans utilized in similar patients. When similar treatment plans are found, they can be reviewed for helpful information. Once such type of helpful information is dosimetry information, which is discussed in more detail below. However, any types of information can be utilized from the similar treatment plans. For example, information on side effects (e.g., toxicities) can be reviewed for prior patients that have similar shape metrics as the new patient to better understand what side effects and to what extent the side effects are a risk.

Figure 1:
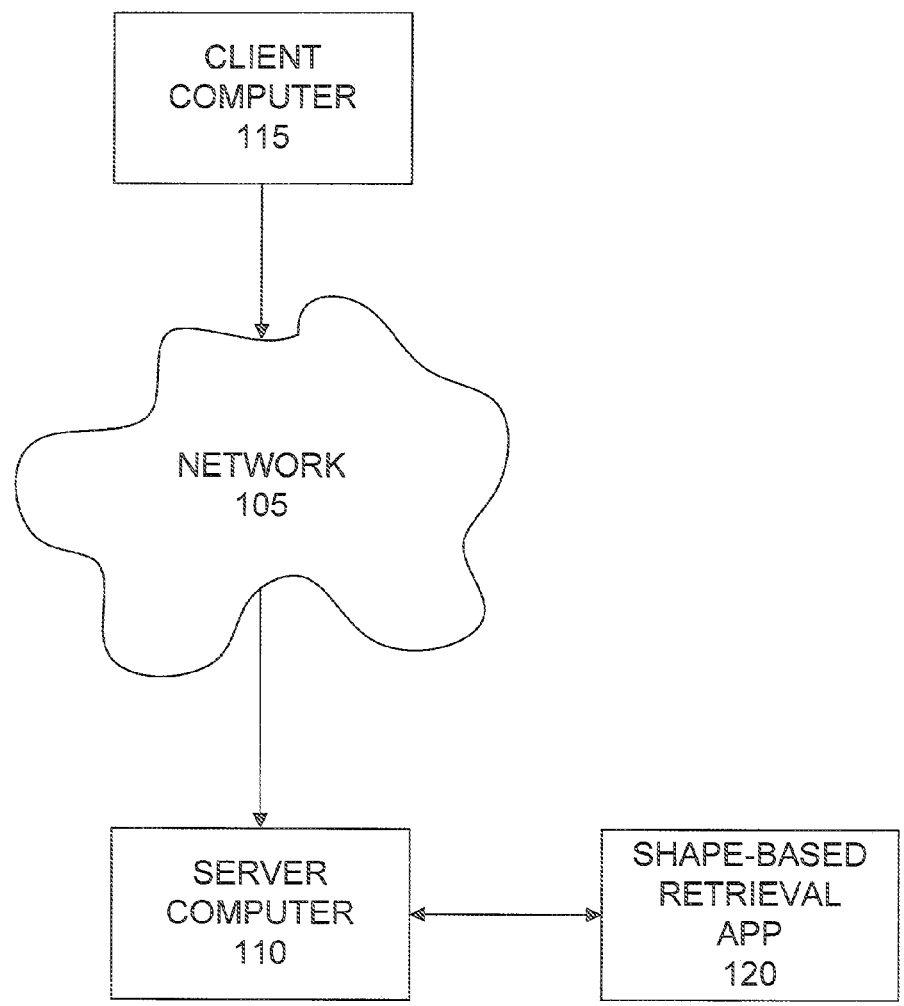
FIGS. 1-2 illustrate a system for determining a therapy treatment plan, according to one embodiment.

FIG. 1 illustrates a system 100 for determining a radiation therapy treatment plan, according to one embodiment. It should be noted that other therapy treatment plans can also be determined in alternate embodiments. The system 100 comprises a client computer 115 connected to a server computer 110 over a network 105 (e.g., Internet, intranet). A shape-based retrieval application 120 can be accessed by the client computer 115 through a server computer 110. Those of ordinary skill in the art will see that some or all modules of the shape-based retrieval application 120 can reside on the server computer, the client computer, or any other computer, or any combination thereof.

Figure 2:
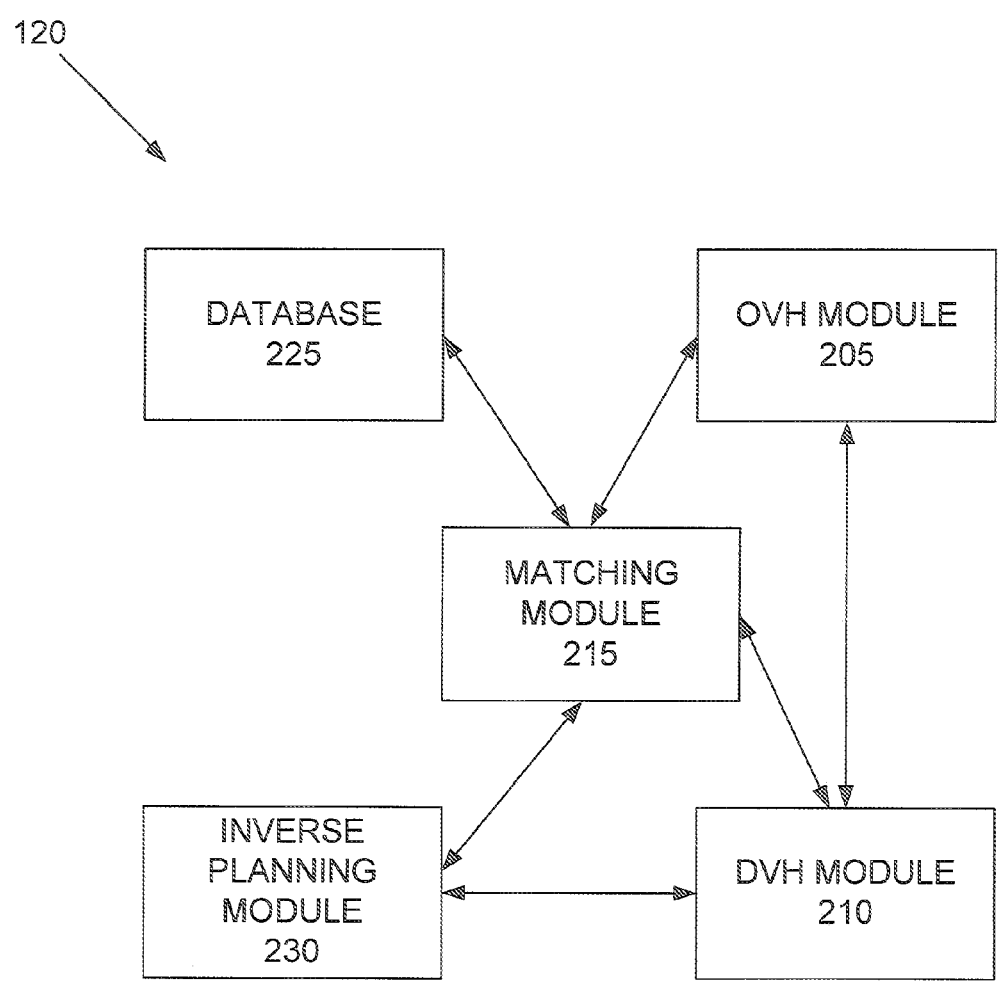

FIG. 2 illustrates details related to the shape based retrieval application 120, according to one embodiment. Shape based retrieval application 120 can comprise: an overlap volume histogram (OVH) module 205, a matching module 215, a database 225, a dose volume histogram (DVH) module 210, and an inverse planning module 230. The OVH module 205 can measure the shape metrics of the new patient. For example, the OAR(s) proximity to at least one target can be measured. It should be noted that other shape metrics can be measured. The database 225 can hold information related to prior patient treatment plans, including OVH information, DVH information, and toxicity information. The matching module 215 can match information from the OVH module 205 to the database 225 in order to retrieve records of prior patients whose shape metrics are similar to the new patient. The DVH module 210 can determine the DVH value utilizing the OVH information. The inverse planning module 230 can utilize parameters, such as the DVH value, as input parameters for inverse planning utilizing at least one intensity-modulated radiation therapy (IMRT).

Figure 3:
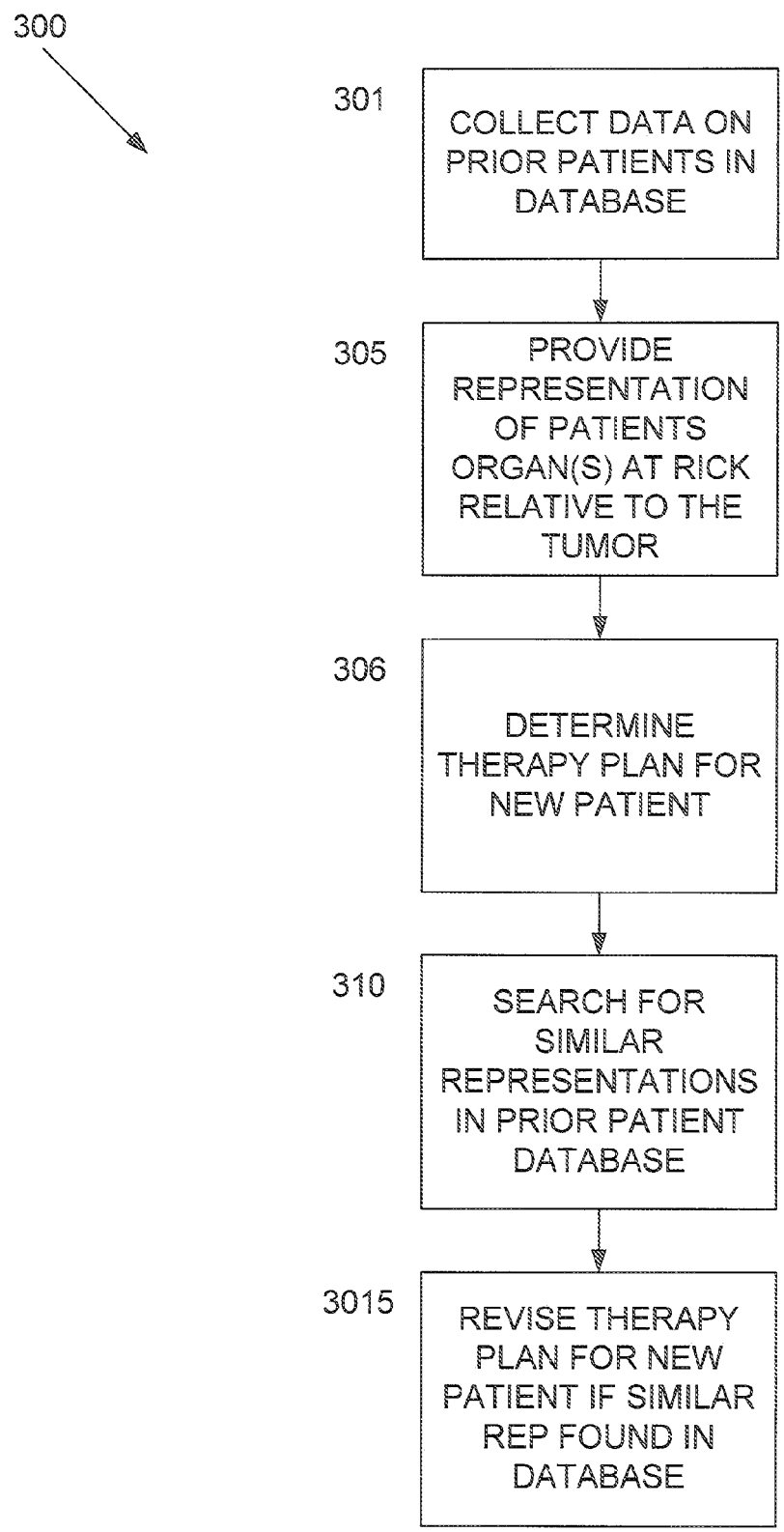
FIGS. 3-4 illustrate a method for determining a therapy treatment plan, according to one embodiment.

FIG. 3 illustrates a method for determining a radiation therapy treatment plan, according to several embodiments. In 301, data from prior patients is collected and stored. In some embodiments, the patients can be identified by the type of cancer.

In 305, a geometric representation of one or more of the new patient's OARs relative to the target (e.g., tumor, various areas targeted to kill various stages of cancer) can be provided. It should be noted that in some embodiments, the tumor and all organs at risk can be determined together. In another embodiment, each organ at risk is determined separately, and the most relevant patient information is found for each organ at risk.

Figure 4:
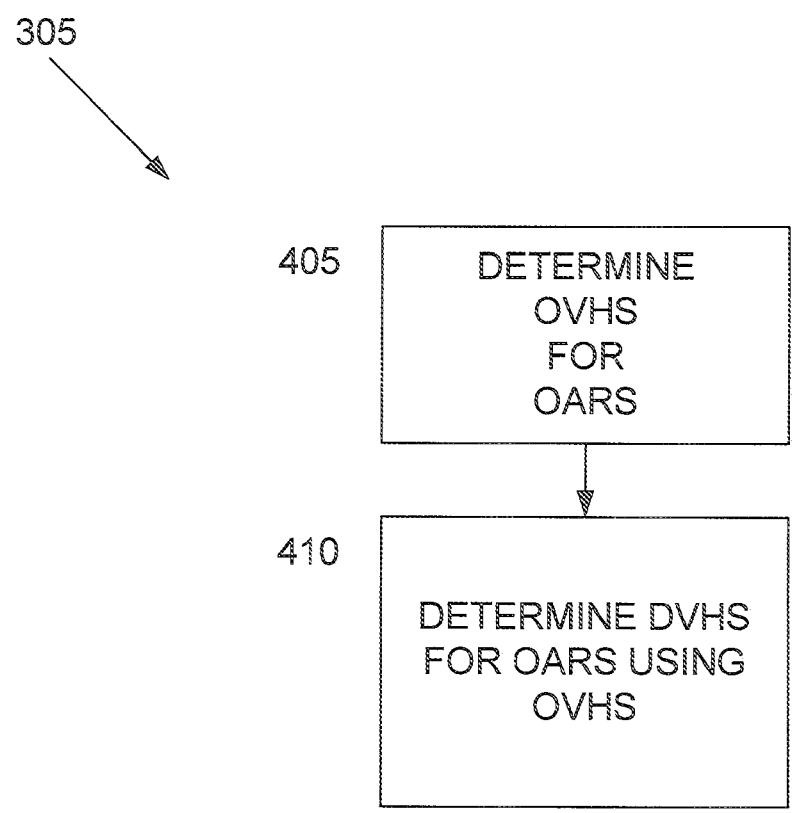

FIG. 4 sets forth details of 305, according to one embodiment. In 405, a shape relationship descriptor, such as, but not limited to, an overlap volume histogram (OVH) can be determined for one or more of the new patient's OARs. The OVH can measure the OAR's proximity to a target. The proximity of the OVH can be distant, proximal, or overlapping with respect to the target. The OVH can also describe the spatial configuration of an organ at risk with respect to a target.

The OVH can be a one-dimensional function giving the percent volume of an OAR that is within a specific distance r from the target:

$$OVH(r) = \frac{|\{p \in O \mid d(p \cdot T) \leq r\}|}{|O|} \qquad \text{(EQUATION 1)}$$

In the above Equation 1, O is the OAR, r is the uniform margin distance around the target T (negative r is contraction, positive r is expansion), p is any location in the OAR, d (p, T) is the signed distance of p from the target's boundary (e.g., negative inside the boundary, positive outside the boundary) and |( )| is the volume of OAR ( ).

Thus, all points (e.g., pixels) in an OAR where the distance from the point to the target boundary is less than r can be found as the volume or size of overlap. This is normalized over the total volume or size of the OAR. If the target is fully encompassing the OAR, this value is 1. If there is no overlap between the target and the OAR, this value is 0. The OVH can thus represent the percentage of the OAR's volume that overlaps with a uniformly expanded or contracted target. The calculation of the OVH can be expressed in two steps: contraction and expansion. In contraction, the target is contracted until there is no overlap between the target and OAR. During contraction, the overlap volume between the contracted target and OAR is calculated. In expansion, the overlap volume between the expanded target and OAR is calculated. Expansion continues until the target fully encompasses the OAR. The resulting curve is the OVH that characterizes the relative spatial configuration of the two shapes. Thus, to be able to determine the full characterization of the shape relationship of the OAR to the target, the OVH needs to be calculated from the point where there is no overlap between the target and the OAR to the point where the target fully encompasses the OAR.

Figure 9:
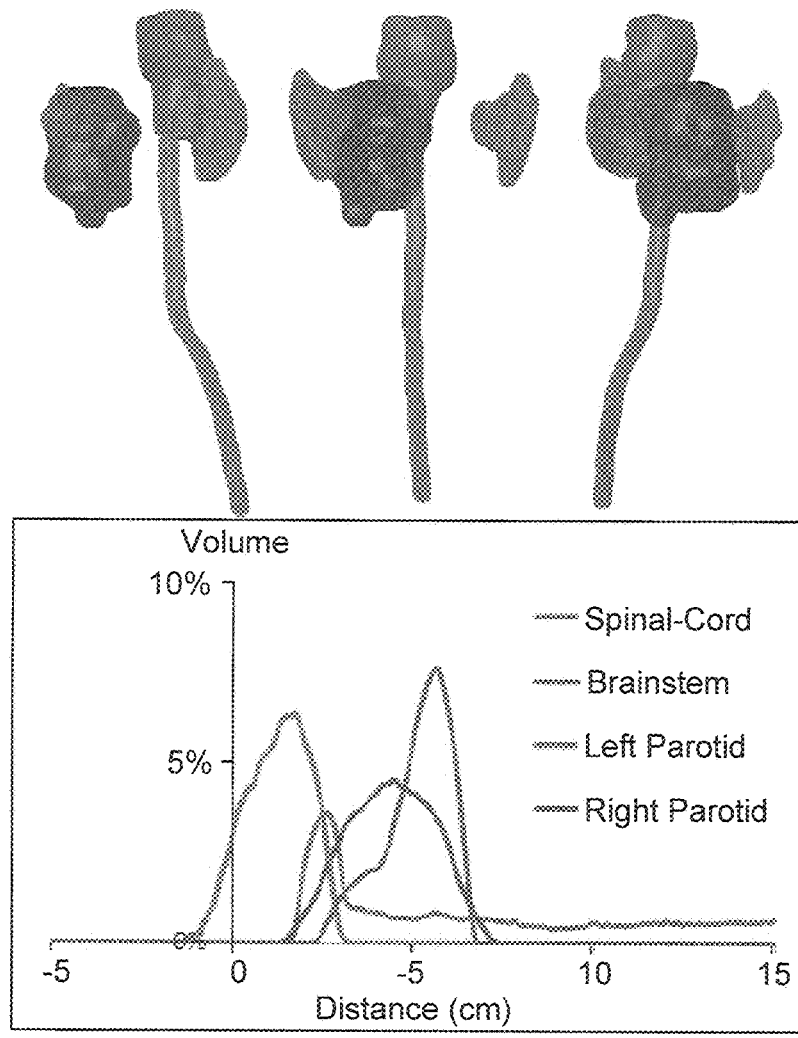

For example, FIG. 9 is an example of a patient's differential OVH descriptors. The image on the left shows the geometry of the tumor volume (black), the spinal cord (red), the brainstem (blue) and the right and left parotid glands (green). By determining the OVH, the properties of the geometric configuration of the organs relative to the tumor can be identified. For example, the fact that the OVH of the left parotid has non-zero values at negative distances can indicate that part of the parotid is overlapped by the tumor volume and therefore it would be difficult to spare the parotid in its entirety. Similarly, since the OVH values for both the spinal-cord and the brainstem are non-zero for distance values smaller than one centimeter, we know that no point on the tumor can be within a centimeter of these organs, so a treatment plan keeping most of the radiation within a centimeter of the tumor is likely to spare them.

Figure 5:
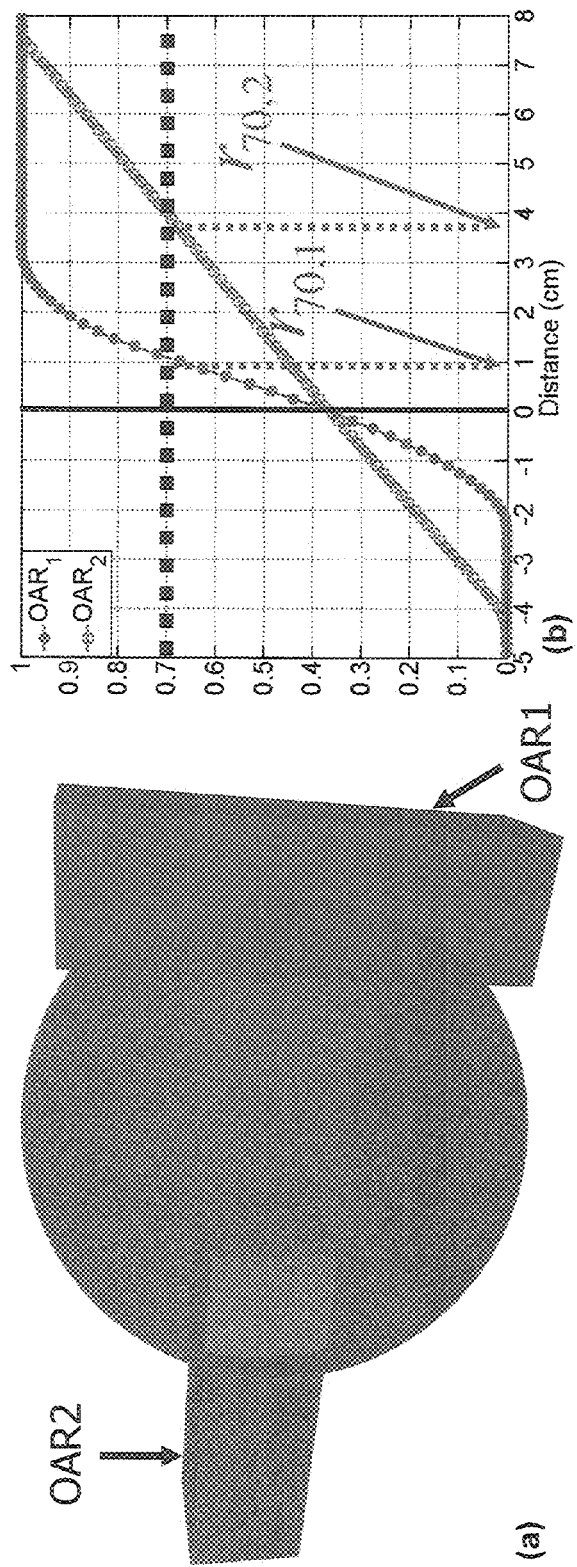
FIGS. 5-10 illustrate various examples of the system and method, according to several embodiments.

As another example, FIG. 5 illustrates a 3-D shape of two OARs and one target. The target is represented by a sphere. The OARS are represented by two rectangular boxes with different spatial relationships with the target. The integral OVH curves of the two OARs relative to the target are illustrated in FIG. 5. FIG. 5 shows that the volumes of the two OARS (e.g. $OAR_1$ and $OAR_2$) within the target are the same: OVH(0)=35.5%.

Figure 7:
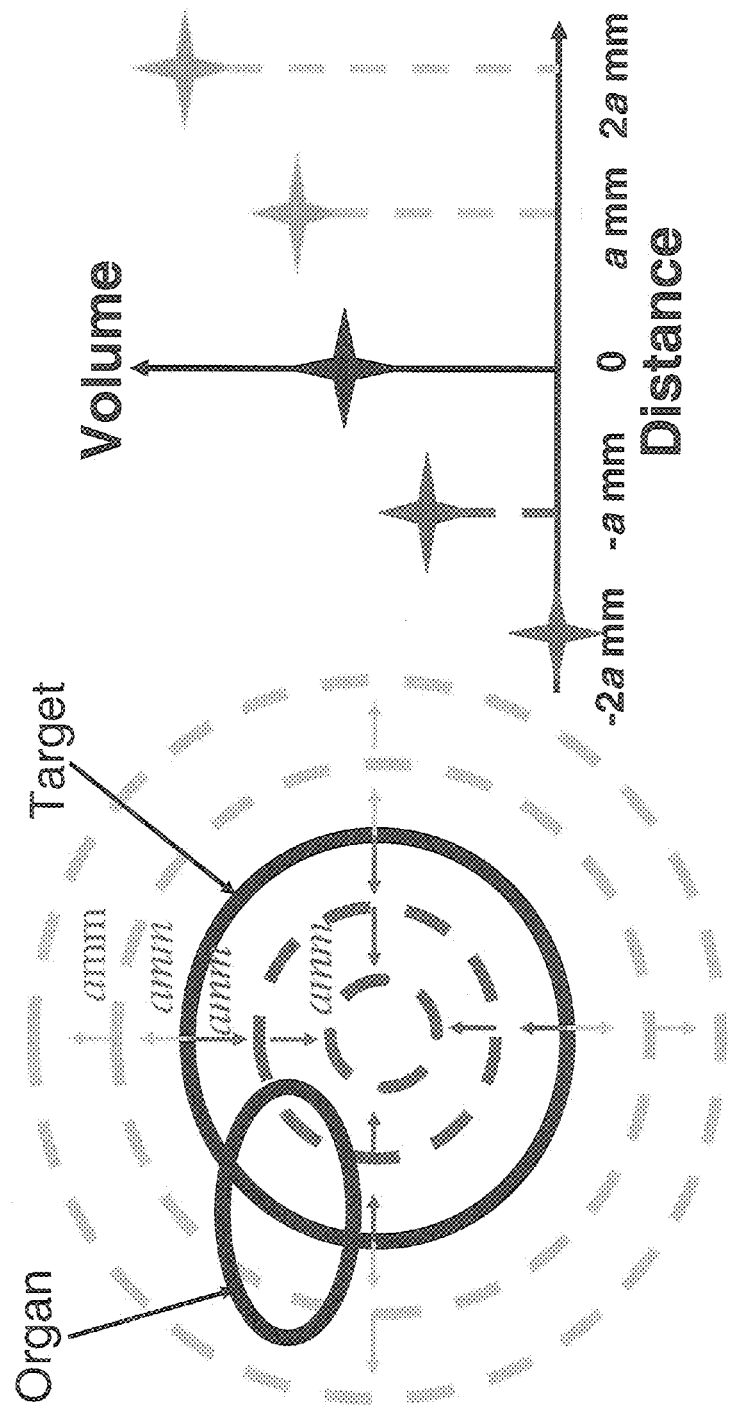

The graph of the OVH curves in FIG. 5 shows that the non-overlapping portion of $OAR_2$ (r>0) is more slowly encompassed by the target (e.g. the OVH shoots up to 1 more slowly) as the target area is expanded, as compared with the non-overlapping portion of $OAR_1$ (e.g., the OVH shoots up to 1 faster). Accordingly, the non-overlapping portion of $OAR_2$ is more easily spared that than of $OAR_1$. However, the OVH curve of $OAR_1$ is much steeper when r<0. This indicates that the overlapping portion of $OAR_1$ is more easily spared than that of $OAR_2$. This can be important, for example, when planning if and how to apply doses to OARS. For example, if an OAR is a serial OAR (e.g., spinal cord), if any portion of the OAR gets a high dose, it can causes serious problems. In contrast, if an OAR is a parallel OAR (e.g., lung), half of the lung can receive a high does and the lung can still function properly. Thus, even though various OARs may have similar shapes, the OVH relationship of OARs to targets can help determine spareability. FIG. 7 illustrates how the OVH can map the shape of an OAR to a volume distance plane by expanding and contracting the target. The yellow represents expansion of the target. The red represents contraction of the target.

Referring back to FIG. 4, in 410, the dose volume histogram (DVH) can be determined. It should be noted that in a conformal (e.g., 3-D) dose distribution, the DVH of an OAR can be directly related to the OVH of that OAR. A conformal dose distribution can be defined by the following properties: 1) the target's boundary is covered by the iso-dose surface (e.g., designating points representing equal points of radiation) of prescription dose $D_p$; 2) any iso-dose surface is an expansion or contraction of the target's boundary; 3) the dose decays monotonically (e.g., consistently decreasing) with distance away from the target's boundary; and 4) the dose grows monotonically (e.g., consistently increasing) with distance inside the target's boundary. In this conformal dose distribution, the larger the expansion distance $r_v$ at percent volume v (i.e., $OVH(r_v)=v$), the easier the OAR is to spare (i.e., the lower the $D_v$ is). The $D_v$ represents the DVH dose at percent volume v (i.e., DVD ($D_v$)=v). This property makes it possible to compare the DVHs of $OAR_1$ and $OAR_2$ based on their OVHS:

$$r_{v,1} \geq r_{v,2} \Rightarrow D_{v,1} \leq D_{v,2} \quad \text{(Equation 2)}$$

In the above Equation 2, $r_{v,1}$ is the expansion distance for $OAR_1$; $r_{v,2}$ is the expansion distance for $OAR_2$; $D_{v,1}$ is the prescription dose for $OAR_1$ and $D_{v,2}$ is the prescription dose for $OAR_2$. For example, applying Equation 2 to the OVH curves in FIG. 5 leads to the following conclusions: for v>OVH (0), we have $D_{v,1}>D_{v,2}$; for v<OVH (0), we have $D_{v,1}<D_{v,2}$; and for v=OVH (0), we have $D_{v,1}=D_{v,2}$ The logic of Equation 2 can thus indicate that if patient 1 had a larger distance from the OAR to the target than patient 2, a lesser dose should be used for patient 1 as opposed to patient 2. Thus, if the new patient is set to be patient 1, all the patients that should be harder to plan (e.g., that have OARs closer to the target area and thus should require larger doses). Then, the patient that utilized the least amount of dosage successfully can be found.

As an alternative, a search can be done for patients that have OVHs similar to the new patients. For example, all patients whose OVH distance(s) of the OAR(s) to the target is close to (e.g., within X amount) the OVH distance(s) of OAR(s) to the target in the new patient, can be found. Then, the patient that utilized the least amount of dosage successfully can be found.

It should be noted that a conformal dose distribution may not be practically achievable due to the irregular shape of targets, the need to spare the OARs, and the inhomogenous densities of patient tissues. However, Equation 2 can still be used to relate the OVH and DVH in non-conformal dose distribution, in, for example, but not limited to, the following circumstances: 1) where planners spend time making the prescription dose conformal to the target; 2) where the target's DVH dose is at 95% volume, $D_{95}$, and $D_{95}$ must be larger than prescription dose $D_p$, (i.e., $D_{95}>D_p$); or 3) where the densities of the target and its surrounding soft tissue are similar; or any combination thereof. (Those of ordinary skill in the art will see that other circumstances are possible where Equation 2 can be used.) As a result, Equation 2 can be used to approximate conformal dose distribution around the target Referring back to FIG. 3, in 306, an initial plan for a new patient can be determined based on the geometric representation.

In 310, the new patients' geometric representation can be used to search the database 225 for prior patients with similar geometric representations. In one embodiment, the DVH and the OVH for the new patient (a query $OAR_q$) can be used to query the database for prior patient(s) with similar values for OVH and DVH. For each patient, the database can store the DVHs of the OARs, the DVHs of the targets, and the OVHs of the OARs. The query can return the set $\{i\}$ of plans for prior patients that satisfy the following conditions for the percent volume v of that OAR's planning goal:

$$\{k\ r_{v,i} \geq r_v\ \text{and}\ D_{v,i} \geq D_v\}$$ (Equation 3)

In the above Equation 3, $r_{v,q}$ is the expansion distance for $OAR_q$; $r_{v,i}$ is the expansion distance for $OAR_i$; $D_{v,q}$ is the prescription close for $OAR_q$ and $D_{v,i}$ is the prescription dose for $OAR_i$. If at least one prior patient's plan meets both conditions of Equation 3, it may be possible to deliver a lower dose to the query OAR, because that prior patient's plan did so. In this case, re-planning may be necessary, as explained in 315 of FIG. 3, to reduce the dose of the query OAR.

Thus, as set forth above, the geometric relationship between the target(s) and OAR(s) of a new patient can be compared with the geometric relationships between the target(s) and OAR(s) of prior patients, whose plans are maintained in database 225. By comparing the geometric configurations, planners can identify those prior patients who have geometric configurations similar to those of the new patient. The treatment plans of the similar prior patients can be retrieved from database 225 and used to guide planners in determining whether at least one dose in at least one new plan for the new patient is appropriate. For example, in one embodiment, a new plan can be compared to an old plan to determine whether a lower dose to an OAR in the new plan can be used. Database 225 can thus serve the function of multiple planners but can claim fewer resources and can offer more efficiency. In addition, the database can enhance experience sharing among planners, such as, but not limited to, inexperienced planners.

Referring, back to FIG. 3, in 315, the most relevant patient information (from one or more patients) can be used to revise the new patient's treatment plan. In one embodiment, an intensity modulated radiation therapy (IMRT) plan can be determined and inverse planning can be done to come up with a revised treatment plan for the new patient. More information on how inverse planning can be determined using, for example, an IMRT, is found in Thomas Bortfeld et al., IMAGE-GUIDED IMRT (2006) and I. J. Das. et al., "Intensity-Modulated Radiation Therapy Dose Prescription, Recording, and Delivery: Patterns of Variability Among Institutions and Treatment Planning Systems", J. Natl. Cancer Inst. 100:5, pp. 300-307 (2008), both of which are herein incorporated by reference.

Figure 10:
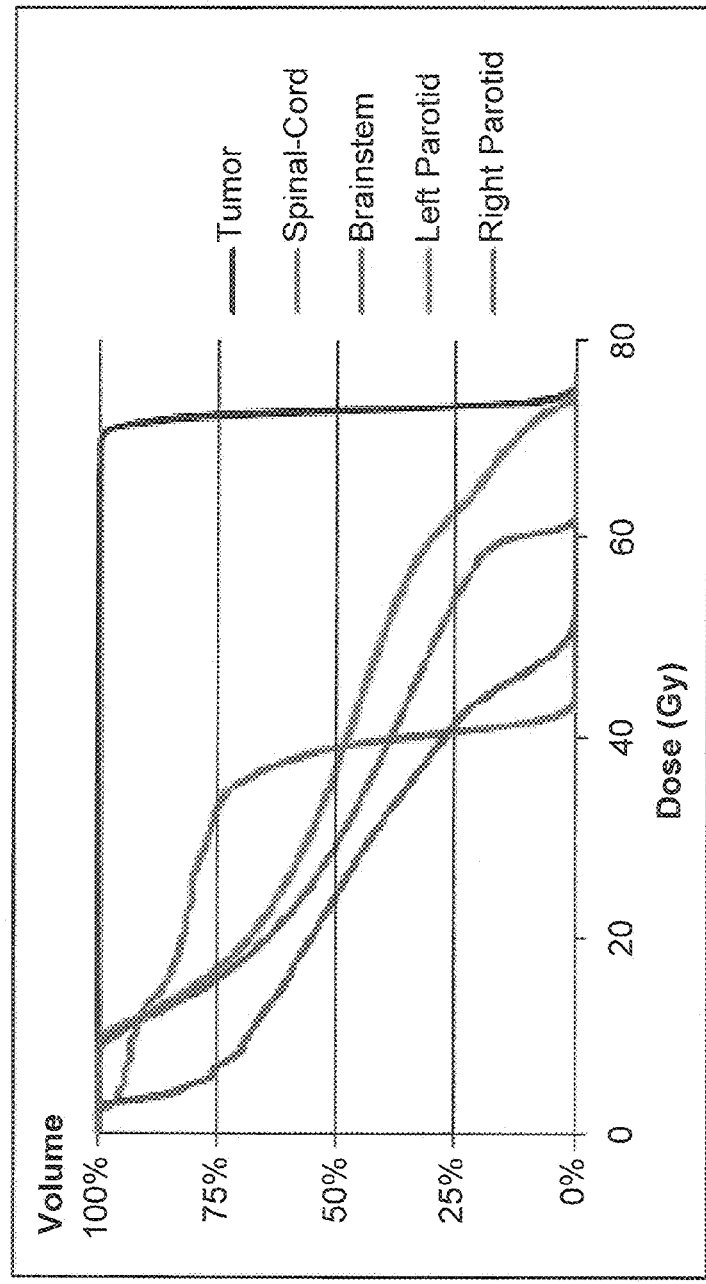

For example, after a treatment plan is designed, a simulation of the IMRT can be performed to determine the resulting dose distribution. The quality of the treatment plan can then be evaluated by utilizing the DVHs of the current plan and previous plans. FIG. 10 illustrates an example of the DVHs derived from the treatment plan for the patient shown in FIG. 9. Since the goal of the treatment is to destroy the tumor, the treatment plan results in a DVH for the tumor that has large values for all doses. For serial organs like the spinal-cord and brain-stem, the goal of the treatment can be to ensure that no part of the organ receives a high dose, and the DVHs for both have zero value beyond 50 Gy. Since the parotids are parallel organs, they remain functional even after a noticeable fraction of their volume has received a high dose, the DVHs for both the left and right parotids show small volumes of the organ receiving doses larger than 55 Gy. Additionally, since the proximity of the left parotid gland to the tumor make it hard to spare, the treatment results in more irradiation of this gland, with 10% of the organ receiving as much as 70 Gy.

The quality of a shape based descriptor can thus be measured by determining the effectiveness with which it retrieves patients having similar DVHs. This can be done by calculating the variation in DVH distances between a patient and the patient's k nearest neighbors (sorted by descriptor similarity). For example, given a new patient, the sum of squared distances from the DVH of the new patient to the DVH of the patient's nearest neighbors can be computed and summed over both the nearest neighbors and the different organs at risk. This can be done for all patients in the database and the sums can be averaged. This can give a 1D distribution of the expected distance of a patient's DVH from the DVH of its k nearest neighbors. Descriptors that better predict DVH similarity can give rise to distributions with smaller expected distances. The best results can thus often be obtained when patients are sorted based on DVH similarity.

EXAMPLES

For example, the parotid DVHs of 32 prior head-and-neck patients can be searched. Each parotid DVH can be queried against the other parotid DVHs to determine whether a lower dose is possible. In one example, 17 parotid DVHs can be flagged as promising the greatest reduction in $D_{50}$ (the DVH does at 50% volume). These 17 parotids can be determined to come from 13 patients. Then, the patient that used the least amount of radiation is determined to be the patient with the most relevant patient information. This most relevant patient information can guide planners in determining whether lower doses delivered to the organs at risk are feasible. In another embodiment, the prior patient with the closest OVH can be determined to be the most relevant prior patient.

A more detailed example follows: Patients with head and neck cancer can be treated by dose painting (an IMRT technique), which can deliver three different prescription doses to the electively irradiated nodal regions and the gross disease sites. In one example, for each patient, three targets can be set: $PTV^L$(low prescription planning target volume)=58.1 Gy; $PTV^M$(medium prescription planning target volume)=63 Gy; and $PTV^H$(high prescription planning target volume)=70 Gy. Correspondingly, each OAR has three OVHs, corresponding to each of the three PTVs.

Figure 6:
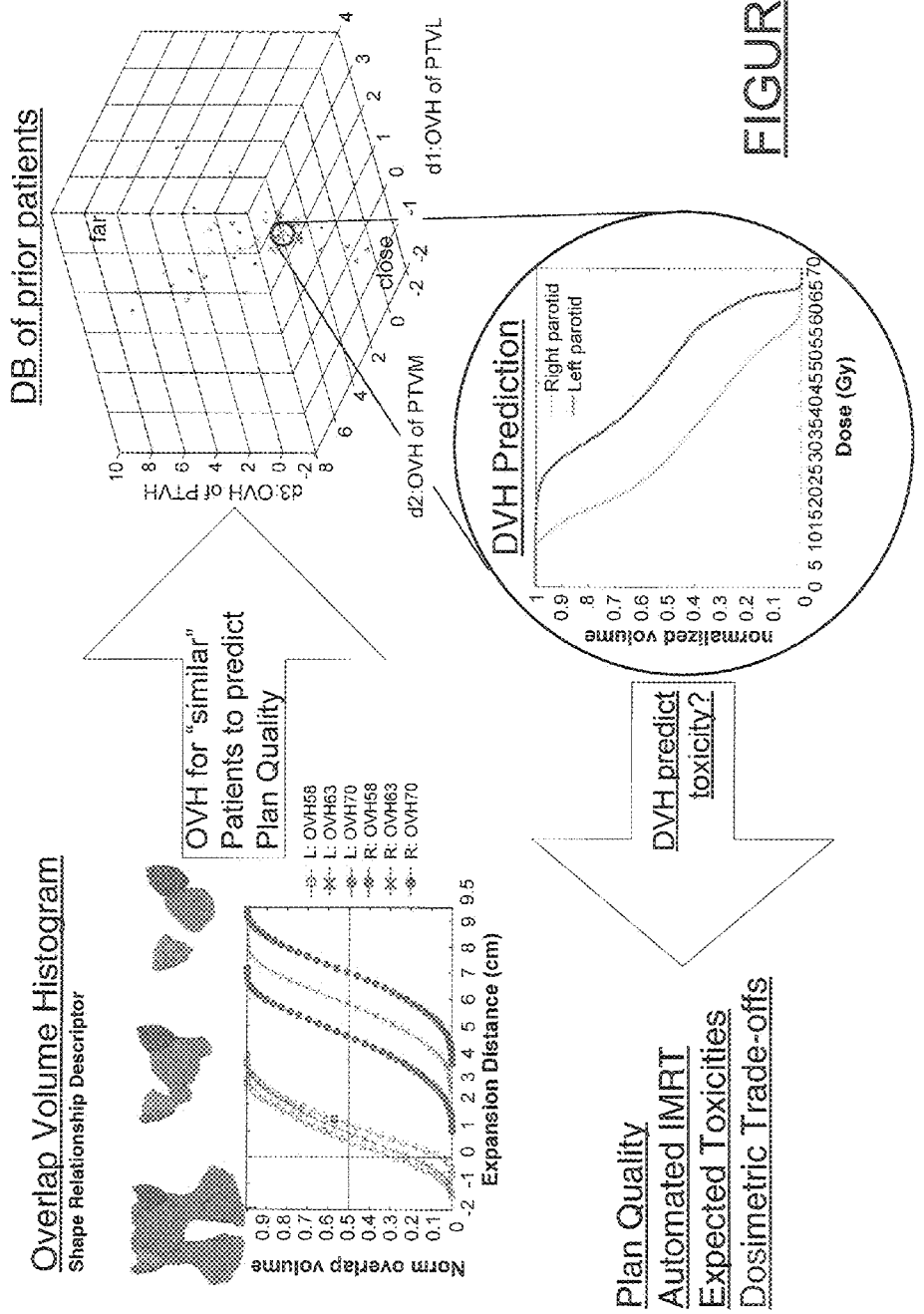

FIG. 6 shows various 3D geometric relationships of the parotid glands of two patients with respect to their three PTVs. The red represents the right parotid gland, the yellow represents the left parotid gland, and the green represents the target. The OVHs can be found for the right and left parotids with respect to the three PTV targets. The DVHs can then be predicted. The database of prior patients can then be searched for similar DVHs.

Figure 8:
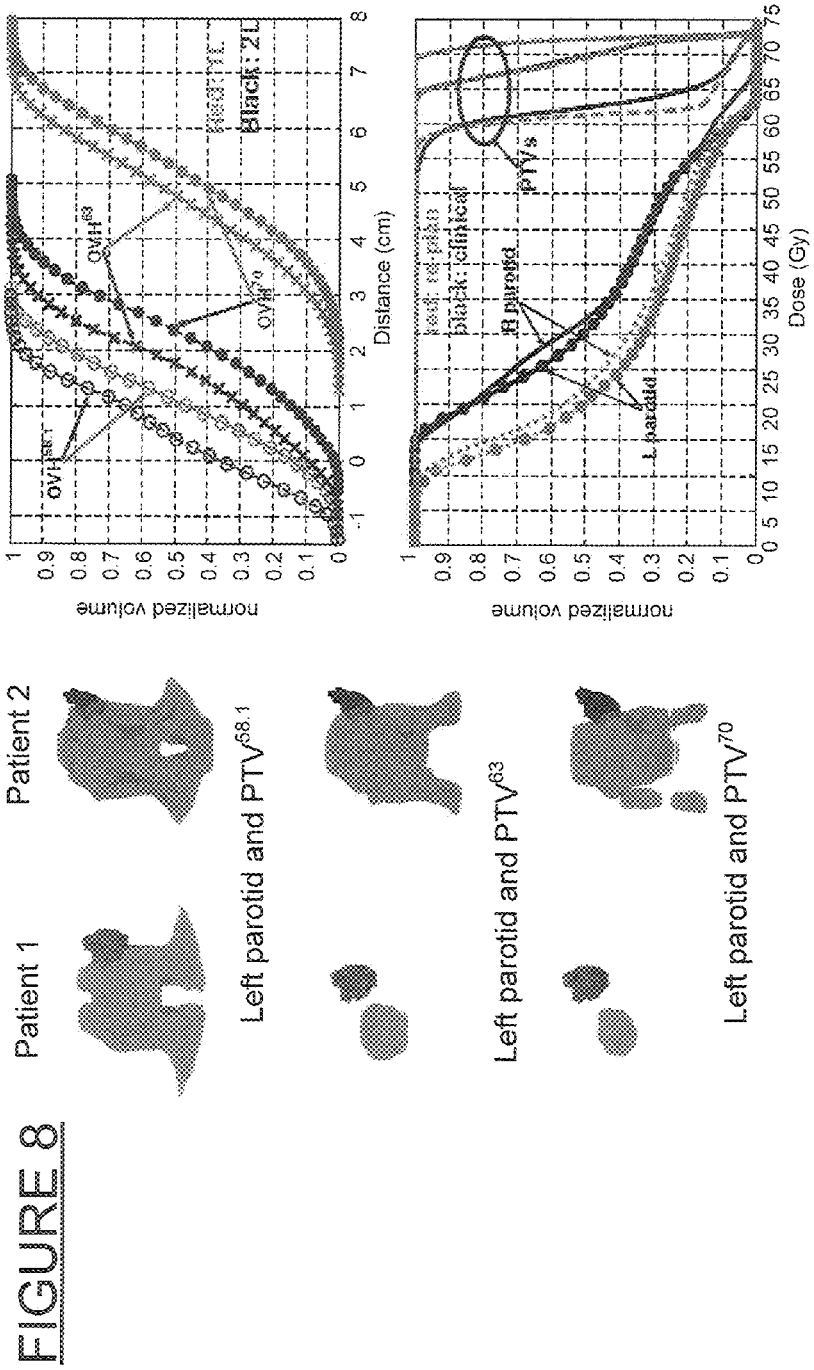

The OVH curves depicting the geometric relationships of the right parotids of two patients with respect to their three PTVs are shown in FIG. 8. The OVH curves illustrate that the distances between the left parotid of patient 1 (1 L) and its three PTVs are larger than the distances between the left parotid of patient 2 (5 L) and its three PTVs for any percent volume v. FIG. 8 also indicates that 2 L is closer to its $PTV^{70}$, since the $OVH^{70}$ curve of 2 L is on the left of the $OVH^{70}$ curve of 2 L for any v.

Applying Equation 2 from above may lead to the conclusion that 1 L should receive a lower dose than 2 L for any v. However, the DVH curves of the left parotids in FIG. 8 show the opposite. This discrepancy indicates that the dose of 1 L can be further reduced, and re-planning for patient 1 may be needed. The re-planning results of patient 1 are detailed below.

CONCLUSION

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described embodiments In addition, it should be understood that any figures which highlight the functionality and advantages, are presented for example purposes only. The disclosed methodology and system are each sufficiently flexible and configurable, such that it may be utilized in ways other than that shown. For example, the steps listed in any flowchart may be re-ordered or only optionally used (even when not explicitly indicated) in some embodiments. Thus, those skilled in the art will realize that the ordering of the steps in FIGS. 3-7 can be altered in other embodiments and that various steps can be removed in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. A method for determining at least one new treatment plan for at least one new patient, comprising:
   providing, utilizing at least one overlap volume histogram (OVH) module, at least one representation of the at least one new patient's at least one organ at risk relative to at least one target;
   searching, utilizing at least one matching module, for at least one prior treatment plan for at least one prior patient with at least one similar representation; and
   reviewing the at least one prior treatment plan for the at least one prior patient in order to determine how to improve the at least one treatment based on information in the at least one prior treatment plan.

2. The method of claim 1, wherein the at least one representation comprises at least one shape metric that captures the geometries of the at least one target and the at least one organ at risk and their configurations relative to each other.

3. The method of claim 1, wherein the at least one representation computes the distribution of distances of points in the at least one organ at risk from the at least one target.

4. The method of claim 3, further comprising:
   defining, utilizing the at least one OVH module, at least one OVH comprising at least one one-dimensional distribution measuring each organ at risk's proximity to the at least one target.

5. The method of claim 4, wherein the at least one OVH is computed as follows:
   using segmented CT scans, computing the volume of the at least one target's signed distance transform for each segment of the target; and
   evaluating the distance transform of the at least one target.

6. The method of claim 4, wherein the following formula is used for the OVH:

$$OVH(r) = \frac{|\{p \in O \mid d(p \cdot T) \le r\}|}{|O|}$$

where OVH(r) is a one-dimensional function giving a percent volume of an organ at risk (OAR) that is within a specific distance r from a target; O is the OAR, r is a uniform margin distance around a target T, p is any location in the OAR, d (p, T) is a signed distance of p from a target's boundary and |O| is a volume of OAR O.

7. The method of claim 4, wherein at least one OVH value is utilized to determine at least one dose volume histogram (DVH) value.

8. The method of claim 7, wherein the at least one DVH value is utilized as at least one input parameter for inverse planning utilizing at least one IMRT.

9. A system for determining at least one new treatment plan for at least one new patient, comprising:
   at least one computer;
   at least one application coupled to the at least one computer, the at least one application configured for:
   providing at least one representation of the at least one new patient's at least one organ at risk relative to at least one target;
   searching for at least one prior treatment plan for at least one prior patient with at least one similar representation; and
   reviewing the at least one prior treatment plan for the at least one prior patient in order to determine how to improve the at least one treatment plan based on information in the at least one prior treatment plan.

10. The system of claim 9, wherein the at least one representation comprises at least one shape metric that captures the geometries of the at least one target and the at least one organ at risk and their configurations relative to each other.

11. The system of claim 9, wherein the at least one representation computes the distribution of distances of points in the at least one organ at risk from the at least one target.

12. The system of claim 11, wherein the at least one application further comprises:
   defining at least one overlap volume histogram (OVH) comprising at least one one-dimensional distribution measuring each organ at risk's proximity to the at least one target.

13. The system of claim 12, wherein the at least one application computes the at least one OVH as follows:
   using segmented CT scans, computing the volume of the at least one target's signed distance transform for each segment of the target; and
   evaluating the distance transform of the at least one target.

14. The system of claim 12, wherein the at least one application utilizes the following formula for the OVH:

$$OVH(r) = \frac{|\{p \in O \mid d(p, T) \leq r\}|}{|O|}$$

where OVH(r) is a one-dimensional function giving a percent volume of an organ at risk (OAR) that is within a specific distance r from a target: O is the OAR, r is a uniform margin distance around a target T, p is any location in the OAR, d (p, T) is a signed distance of p from a target's boundary and |O| is a volume of OAR O.

15. The system of claim 12, wherein the at least one application utilizes the at least one OVH value to determine at least one dose volume histogram (DVH) value.

16. The system of claim 15, wherein the at least one application utilizes the at least one DVH value as at least one input parameter for inverse planning utilizing at least one IMRT.

17. The method of claim 1, further comprising: determining whether delivering at least one lower dose to the at least one organ at risk is feasible.

18. The system of claim 9, wherein the at least one application is further configured for determining whether delivering at least one lower does to the at least one organ at risk is feasible.

* * * * *